United States Patent
Rao et al.

(10) Patent No.: US 10,435,664 B2
(45) Date of Patent: *Oct. 8, 2019

(54) SYSTEM AND METHOD FOR PRODUCTION OF ON-DEMAND PROTEINS IN A PORTABLE UNIT FOR POINT OF CARE DELIVERY

(71) Applicant: University of Maryland, Baltimore County, Baltimore, MD (US)

(72) Inventors: Govind Rao, Ellicott city, MD (US); Yordan Kostov, Columbia, MD (US); Leah Tolosa, Columbia, MD (US); Xudong Ge, Woodstock, MD (US); Douglas Frey, Ellicott City, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,609

(22) Filed: Apr. 30, 2018

(65) Prior Publication Data

US 2018/0298325 A1 Oct. 18, 2018

Related U.S. Application Data

(63) Continuation of application No. 15/095,305, filed on Apr. 11, 2016, now Pat. No. 9,982,227, which is a continuation-in-part of application No. 13/823,911, filed as application No. PCT/US2012/028358 on Mar. 8, 2012, now Pat. No. 9,388,373.

(60) Provisional application No. 61/450,191, filed on Mar. 8, 2011.

(51) Int. Cl.
*C07K 9/00* (2006.01)
*C12M 1/00* (2006.01)
*C12M 1/34* (2006.01)

(52) U.S. Cl.
CPC ............ *C12M 47/10* (2013.01); *C12M 41/12* (2013.01); *C12M 47/12* (2013.01)

(58) Field of Classification Search
None
See application file for complete search history.

(56) References Cited

U.S. PATENT DOCUMENTS

| | | |
|---|---|---|
| 5,968,767 A | 10/1999 | Sheikh et al. |
| 6,642,024 B1 * | 11/2003 | Pennica ............ C07K 14/47 435/252.3 |
| 6,670,173 B1 | 12/2003 | Schels et al. |
| 6,673,532 B2 | 1/2004 | Rao |
| 6,905,843 B1 | 6/2005 | Endo et al. |
| 6,946,075 B2 | 9/2005 | Kopf |
| 7,041,493 B2 | 5/2006 | Rao |
| 7,485,454 B1 | 2/2009 | Jury et al. |
| 9,163,272 B2 | 10/2015 | Park et al. |
| 9,982,227 B2 | 5/2018 | Rao et al. |
| 2008/0269468 A1 | 10/2008 | Vogel et al. |
| 2008/0287656 A1 | 11/2008 | Peters et al. |
| 2009/0178495 A1 | 7/2009 | Steigmiller et al. |
| 2010/0298172 A1 | 11/2010 | Desmond et al. |
| 2011/0065084 A1 | 3/2011 | Rao et al. |
| 2013/0280797 A1 | 10/2013 | Rao et al. |

FOREIGN PATENT DOCUMENTS

| | | |
|---|---|---|
| WO | 2005063808 A1 | 7/2005 |
| WO | 2016019350 A2 | 2/2016 |

OTHER PUBLICATIONS

Pierce (Protein stability and Storage, Technical resource, 2005, updated Jul. 14, 2015).*

Salehi, Amin S. et al. "Cell-free protein synthesis of a cytotoxic cancer therapeutic: Onconase production and a just-add-water cell-free system." Biotechnology Journal, 2015, doi.1002/biot. 201500237.

Sun, Zachary et al. "Protein degradation in a TX-TL cell-free expression system using ClpXP protease." Technical Report, Jul. 8, 2014, http://www.cds.caltech.edu/~murray/papers/sksm14-clpxp.html.

* cited by examiner

*Primary Examiner* — Jeanette M Lieb
(74) *Attorney, Agent, or Firm* — Tristan A. Fuierer; Marianne Fuierer; Olive Law Group, PLLC

(57) ABSTRACT

A portable and mobile bioprocessing system and method for protein manufacturing that is compact, integrated and suited for on-demand production of any type of proteins and for delivery of the produced proteins to patients or for assay purposes. The portable system and method can also be used for efficient on-demand production of any type of protein with point-of-care delivery.

21 Claims, 15 Drawing Sheets

SYSTEM AND METHOD FOR PRODUCTION OF ON-DEMAND PROTEINS IN A PORTABLE UNIT FOR POINT OF CARE DELIVERY

CROSS REFERENCE TO RELATED APPLICATIONS

This application is a divisional of U.S. patent application Ser. No. 15/095,305 filed on Apr. 11, 2016, now U.S. Pat. No. 9,982,227, as issued on May 29, 2018, which is a continuation-in-part application of U.S. patent application Ser. No. 13/823,911, filed on Jun. 28, 2013, now U.S. Pat. No. 9,388,373, which in turn was a 371 application of PCT Application No. PCT/US2012/028358, filed on Mar. 8, 2012, which in turn claims priority to U.S. Provisional Application Ser. No. 61/450,191, filed Mar. 8, 2011, the contents of all is hereby incorporated by reference herein for all purposes.

GOVERNMENT RIGHTS IN INVENTION

This invention was made with government support under Grant Number N66001-13-C-4023 awarded by the Defense Advanced Research Projects Agency (DARPA). The government has certain rights in the invention.

BACKGROUND OF THE INVENTION

Field of the Invention

The present invention relates to protein manufacturing and, more particularly, to an integrated and compact bioprocessing system for on-demand production or manufacturing of proteins for point-of-care delivery.

Background of the Related Art

The time it takes for a new drug to reach the market is 8-10 years at a cost approaching $1.2 billion. Many of these new drug entities are referred to as biologics (e.g., a protein used as a drug or therapeutic). These are molecules produced by living cells in vitro using cell culture and fermentation technologies. Stringent process control is required since changes in culture conditions can lead to, for example, altered glycosylation profiles, which can then drastically change the drug's pharmacokinetics, efficacy and immunogenicity. Therefore, much effort towards FDA approval is devoted to the development of documented and robust manufacturing processes that will produce safe and efficacious biologics of consistent quality. These are collectively referred to as good manufacturing processes (GMP). The goal is to arrive at a process that is well defined and reproducible, and that leads to products that meet predetermined characteristics of quality, identity, purity, safety and efficacy.

Biologics are currently produced in a centralized manufacturing facility with large scale (>10,000 liters) cell cultures, and with the necessary large volume separation, purification, formulation, packaging, and distribution infrastructure (e.g. a typical Merck, Pfizer or Genentech plant). The time period from a cell bank to the final delivery of the therapeutic vial is on the order of 6-8 weeks under ideal conditions and produces batches of around 10 Kg bulk protein. As shown in FIG. 1, the process itself is complex. FIG. 1 shows a typical flow sheet for the manufacturing of protein biologics—both for proteins that are expressed intracellularly and proteins expressed extracellularly. Every step needs to be individually developed, scaled-up, optimized and validated in a manufacturing setting. The final product will also have an expiration date and is either shipped lyophilized or via a cold chain, which must also be documented.

Thus, there is a need for production of biological medicines in real-time and/or on-demand to provide therapeutic proteins in remote locations. Also, there is a need for a system and method of preparing therapeutic proteins with increased activity with the possibility of reduced amount of preservation, enhancing and/or stabilizing excipients because of the immediate and/or timely use of such therapeutic proteins.

A similar opportunity exists for proteins in non-therapeutic applications. By their nature, proteins are unstable and require preservation by a variety of methods to preserve their activity. They are widely used in the diagnostics industry, in food and cosmetics. In these cases as well, the ability to manufacture fresh protein on-demand would be of great benefit.

SUMMARY OF THE INVENTION

The present invention provides for an integrated and compact bioprocessing system and method for the production of proteins with increased activity with the possibility of reduced amount of preservation, enhancing and/or stabilizing excipients because of the immediate and/or timely use of therapeutic proteins and diagnostic proteins, where a critical assay is to be performed.

In one aspect, the present invention provides a portable and compact bioprocessing system for the production of proteins for point-of-care delivery.

In another aspect, the present invention provides for an integrated and compact bioprocessing system for protein expression and purification.

In yet another aspect, the present invention provides for a method for on-demand production and delivery of a therapeutic protein to a patient.

In a still further aspect, the present invention provides for a portable system and method for on-demand production of a therapeutic protein prepared in a composition with reduced amounts of stabilizers, oxidation/reduction agents and/or other excipients.

In another aspect, the present invention provides for a portable system and method for on-demand production of a therapeutic protein, wherein the therapeutic protein exhibits increased potency due to the timely synthesis and substantially immediate delivery of protein. Preferably, the newly synthesized proteins are delivered to a patient within one hour, to one day, to two weeks. Preferably any refrigeration is at a temperature above freezing from 0 to 6° C. Any freezing of the proteins is preferably a single event with temperatures ranging from about −2° C. to about −10° C.

In yet another aspect, the present invention provides for a portable system and method for on-demand production of a therapeutic protein, wherein the produced therapeutic protein can be delivered continuously or as a bolus as it is produced and as it happens physiologically, where the body produces needed proteins over an extended time in vivo and when needed.

A still further aspect, the present invention provides for a freshly synthesized protein in a composition, wherein the freshly synthesized protein is synthesized on-demand and exhibits increased activity, and wherein a buffering composition comprising the freshly synthesized protein is essentially lacking a stabilizer.

To achieve at least the above aspects, in whole or in part, there is provided a bioprocessing system comprising a production module for producing a protein and a purification module for receiving the protein from the production module and for purifying the protein from reagents. The bioprocessing system may further comprise a processor for controlling and/or monitoring at least the production module and/or the purification module. The processor is communicatively connected to at least the production module and/or purification module to control the timing, temperature and other parameters necessary for optimizing the production and purification of the synthesized proteins to provide a sufficient amount of or a therapeutic dosage of the synthesized protein. Such length of time in the production module and/or purification module may be used to affect the potency and/or activity of the synthesized protein.

To achieve at least the above aspects, in whole or in part, there is also provided a bioprocessing system, comprising a reactor for protein expression, a membrane chromatography component for receiving and purifying protein output by the reactor and a diafiltration component for receiving purified protein from the membrane chromatography and for further purifying the purified protein.

Additional advantages, aspects, and features of the invention will be set forth in part in the description which follows and in part will become apparent to those having ordinary skill in the art upon examination of the following or may be learned from practice of the invention. The aspects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The present invention is particularly suited for the on-demand manufacturing of therapeutic proteins (either cell-based or cell-free) that are suitable for direct delivery to a patient. Therefore, the present invention will be primarily described and illustrated in connection with the manufacturing of therapeutic proteins. However, the present invention can also be used to manufacture any type of protein, including toxic proteins, proteins with radiolabeled amino acids, unnatural amino acids, etc. Further, the present invention is particularly suited for the on-demand manufacturing of proteins using cell-free expression, and thus the present invention will be described primarily in the context of cell-free protein expression. However, the present invention can also be used in connection with cell-based protein expression.

Figure 1:
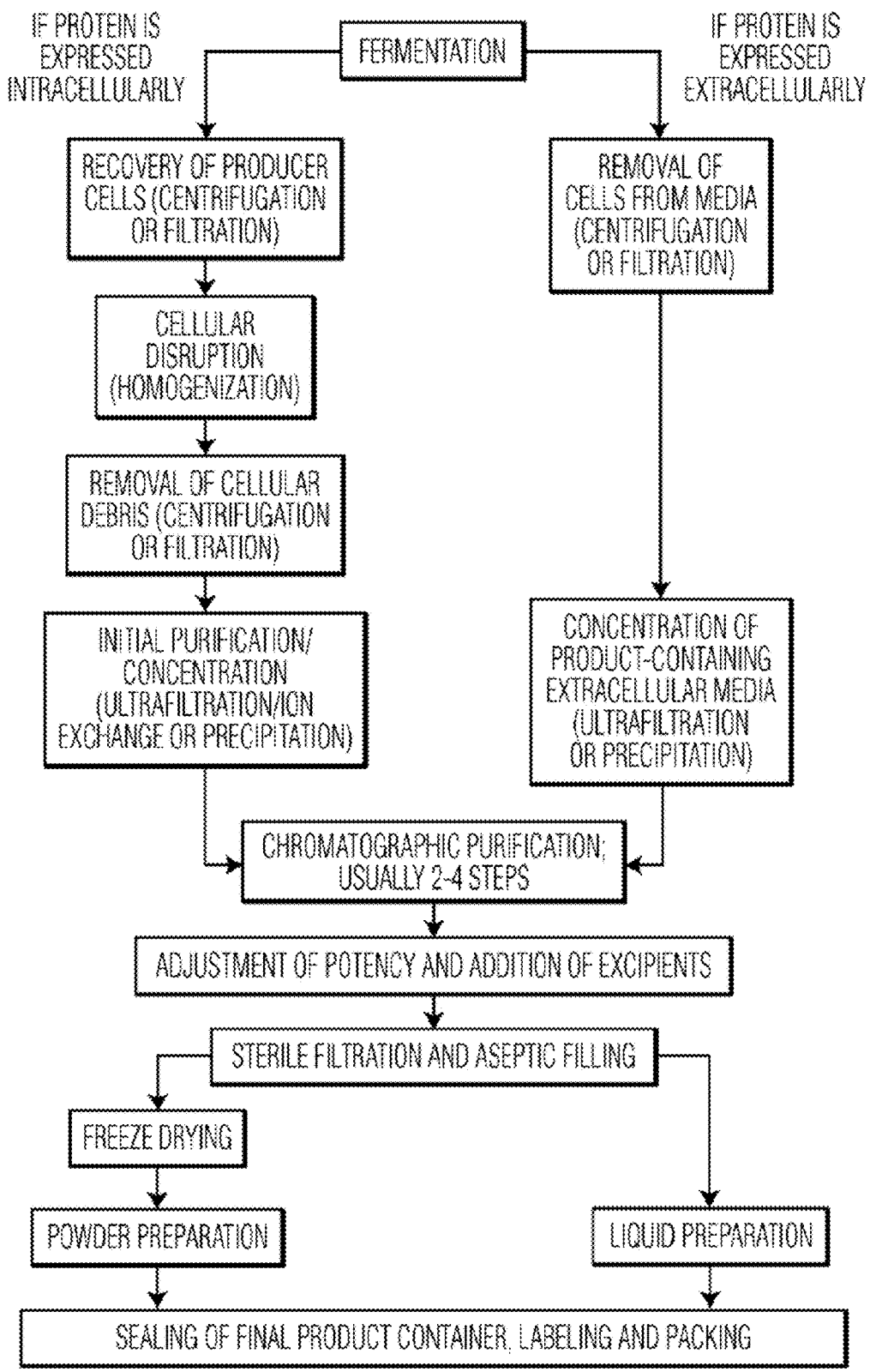
FIG. 1 shows a typical flow sheet for the manufacturing of protein biologics, both for proteins that are expressed intracellularly and proteins expressed extracellularly.
Figure 2:
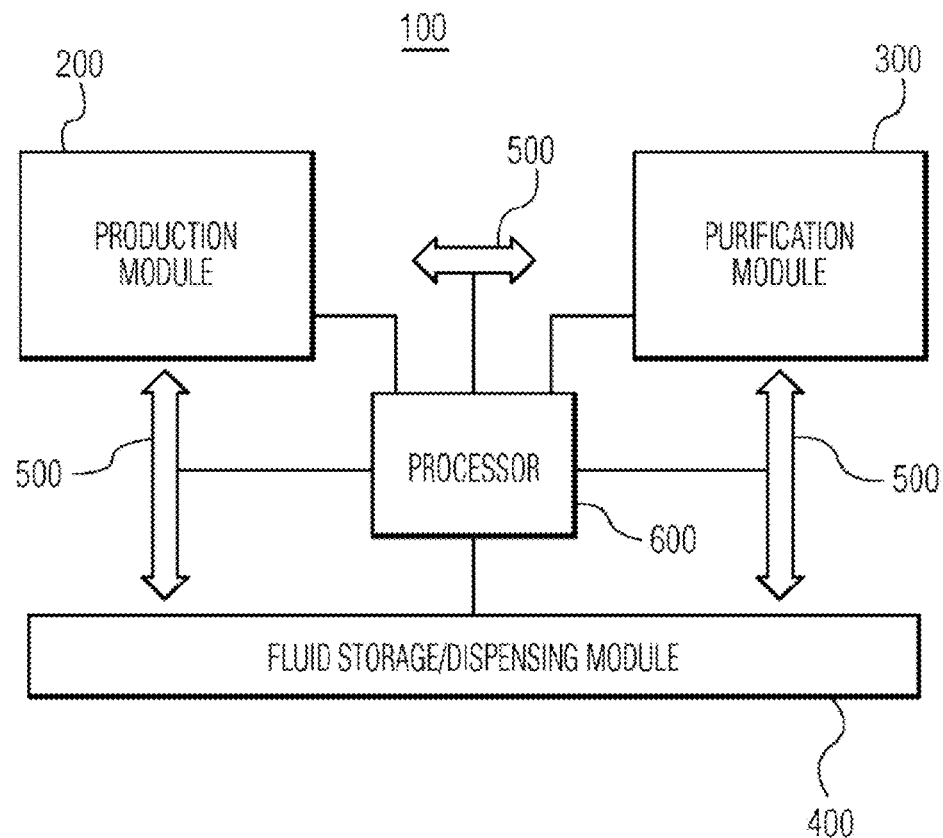
FIG. 2 is a block diagram that illustrates the principles of operation of one preferred embodiment of the present invention.

FIG. 2 is a block diagram that illustrates the principles of operation of one preferred embodiment of the present invention. The bioprocessing system 100 includes a production module 200, a purification module 300 and a fluid storage/dispensing module 400 that are fluidly coupled via coupling components 500. A processor 600 may be in electrical communication with one or more of the production module 200, purification module 300, coupling components 500 and fluid storage/dispensing module 400 for controlling and monitoring the operation of the system 100.

The fluid storage/dispensing module 400 is adapted to store the solutions needed for the production of a protein. The fluid storage/dispensing module 400 may also include containers for storing any waste product produced during the production of the protein. The fluid storage/dispensing module 400 may be temperature controlled, if needed, to maintain the solutions at a required temperature.

The production module 200 is adapted to receive the solutions required for production of a protein, such as a therapeutic protein, from the fluid storage/dispensing chamber via coupling components 500. The production module 200 may suitably include a bioreactor adapted for maintaining living cells that incorporates non-invasive optical chemical sensing technology for monitoring culture parameters (e.g., pH, oxygen, optical density, fluorescence, absorbance, redox, temperature, etc.), such as the bioreactors and optical chemical sensing technology illustrated and described in commonly assigned and related U.S. Pat. Nos. 6,673,532 and 7,041,493, as well as co-pending commonly assigned and related patent application Ser. No. 12/991,947, whose disclosures are incorporated by reference herein in their entirety. These types of bioreactors are particularly suited for cell-based production of therapeutic proteins. Alternatively, the production module 200 may suitably include a stirred mini-reactor such as, for example, the BioGenie Minibioreactor sold by Scientific Bioprocessing, Inc., that is adapted for the cell-free production of a protein, and that are also equipped with sensors for monitoring reaction parameters (e.g., pH, oxygen, optical density, fluorescence, absorbance, redox, temperature, etc.).

The production module 200 as illustrated in FIG. 2 is designed for batch mode protein production where all the components for protein production (DNA, cell-free lysate, reaction buffer, etc.) are combined in a single step and then delivered to the purification module via coupling components 500 at the end of the reaction (3-6 hours). The production module 200 may also be a cup with a dialysis membrane bottom or a dialysis cassette with dialysis membrane on both sides. The cup or cassette will be surrounded by a dialysis buffer to remove reaction waste products such as inorganic phosphate, but also to maintain the concentration of nutrients such as amino acids and creatine phosphate. The solutions for protein production are delivered to the dialysis cup or the dialysis cassette and the surrounding dialysis buffer from the fluid storage/dispensing chamber 400 via coupling components 500.

After the reaction is complete, the raw product is then transferred to the purification module 300 via coupling components 500. The purification module 300 contains the necessary purification components for purifying the protein from the reagents. The purification module 300 can include, for example, chromatography components and dialyses components for purifying the biologic.

The production module 200 and the purification module 300 may each include sensors for monitoring reaction parameters and/or product quality parameters. The parameters monitored can include, but are not limited to, conductivity, temperature, pH, oxygen and $CO_2$. The sensors may be any type of invasive sensor known in the art for monitoring these parameters, where the sensors are in contact with the process fluid. In addition, the sensors may be non-invasive optical chemical sensors, such as those described in U.S. Pat. Nos. 6,673,532 and 7,041,493, and U.S. patent application Ser. No. 12/991,947. In addition, spectrometers known in the art can be used in the production module 200 and/or the purification module 300 to monitor the product stream and/or the inputs to each module. The parameters measured by such spectrometers can include, but are not limited to, absorbance, fluorescence, Raman scattering, circular dichroism and infrared spectral characteristics.

Figure 3:
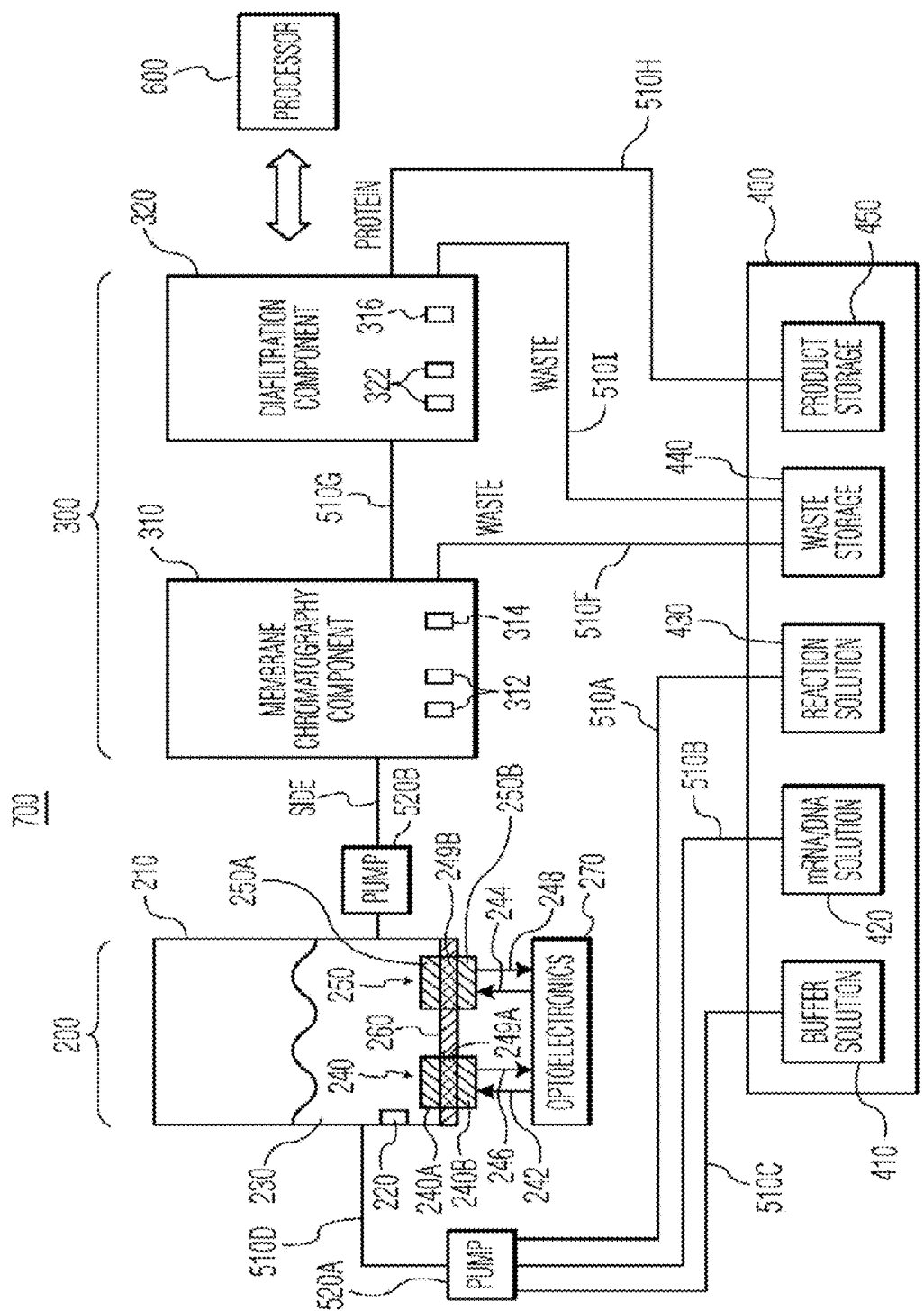
FIG. 3 is a schematic diagram of a bioprocessing system, in accordance with another preferred embodiment of the present invention.

FIG. 3 is a schematic diagram of a bioprocessing system 700, in accordance with another preferred embodiment of the present invention. The system 700 is particularly suited for the cell-free production of proteins and will be described in this context.

The system 700 includes a reactor 210, in which protein expression takes place, a membrane chromatography component 310, a diafiltration component 320 and a fluid storage/dispensing module 400. The reactor 210 preferably includes a heating and cooling element 220, suitably a thermoelectric cooler, for controlling the temperature of the solution 230 inside the reactor 210. The reactor also preferably includes sensors 240 and 250 for monitoring parameters in the reactor solution 230, such as pH, oxygen, redox, conductivity or any other parameter that can be measured with existing sensors. The sensors 240 and 250 can be implemented with any type of sensor known in the art for measuring the desired parameters. However, the sensors 240 and 250 are preferably non-invasive optical chemical sensors.

The system 700 also includes a processor 600 that is in communication with one or more of the reactor 210, optoelectronics 270, membrane chromatography component 310, diafiltration component 320, fluid storage/dispensing module 400 and pumps 520A and 520B for controlling and/or monitoring the operation of the system 700.

Optoelectronics 270 are provided for exciting the optical chemical sensors 240 and 250 with excitation light 242 and 244, respectively, and for receiving and detecting emission light 246 and 248 from the optical chemical sensors 240 and 250, respectively. As discussed above, commonly assigned and related U.S. Pat. Nos. 6,673,532 and 7,041,493, as well as co-pending commonly assigned and related U.S. patent application Ser. No. 12/991,947 describe in more detail how non-invasive optical chemical sensing technology can be used to monitor parameters.

In FIG. 3, two optical chemical sensors 240 and 250 are shown, and are preferably adapted to measure pH and dissolved oxygen, respectively. However any number of optical chemical sensors (including only one) may be used depending on the number and type of parameters being measured. Optoelectronics 270 include optical excitation sources (not shown) for generating the excitation light 242 and 244, as well as photodetectors (not shown) for detecting the emission light 246 and 248 from the optical chemical sensors 240 and 250. The type of optical excitation source or sources are the types used in optoelectronics. Any combination of optical excitation sources and optical chemical sensors may be used, depending on the number and types of parameters being measured. Examples of optical excitation sources that can be used included in optoelectronics 270 include, but are not limited to, light emitting diodes and laser diodes. Alternatively, the optoelectronics 270 may just be used to measure optical properties of the reactor contents in their entirety absent any sensors.

Further, for each optical chemical sensor 240 and 250, two possible placements on the reactor 210 are shown. The two possible placements for optical chemical sensor 240 are shown as 240A and 240B. The two possible placements for optical chemical sensor 250 are shown as 250A and 250B. The use of other non- contact sensors (i.e. Raman, contact free conductivity sensors etc) is also possible in this context.

In the "A" placement (240A and 250A), the optical chemical sensors 240A and 250A are positioned inside the reactor 210 on a reactor wall 260. With this placement, the optical chemical sensors 240A and 250A are in physical contact with the solution 230, and the reactor wall 260 on which the optical chemical sensors 240A and 250A are placed is optically transparent to the excitation light 242 and 244, so that the excitation light can reach the optical chemical sensors 240A and 250A.

In the "B" placement (240B and 250B), the optical chemical sensors 240B and 250B are positioned outside the reactor 210 on reactor wall 260. With this placement, the thickness of the reactor wall 260 is sufficiently small so as to allow the analytes that are being measured to diffuse through the reactor wall 260 and contact the optical chemical sensors 240B and 250B. Alternatively, the portions of the reactor wall 260 on which the optical chemical sensors 240B and 250B are attached can be replaced with barrier membranes 249A and 249B that are adapted to allow the analytes being measured to diffuse through so that they come in contact with optical chemical sensors 240B and 250B. The use of barrier membranes and thin reactor walls to effectuate diffusion of the analytes of interest through a container wall to optical chemical sensors is described in more detail in commonly assigned and related U.S. patent application Ser. No. 13/378,033, which is incorporated herein by reference in its entirety.

In the FIG. 3 embodiment, the fluid storage/dispensing module 400 preferably includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. In operation, reaction solution, mRNA/DNA solution and buffer solution are directed to reactor 210 via conduits 510A, 510B, 510C and pump 520A.

After the reaction in the reactor 210, the raw product is directed to membrane chromatography component 310 via conduit 510E and pump 520B for purification of the protein from the reagents. Membrane chromatography component 310 may suitably include a cylindrically shaped housing which contains porous membrane layers (preferably at least 10 porous membrane layers), where the individual membranes consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography. One preferred embodiment of the membrane chromatography component 310 will be discussed in more detail below in connection with FIG. 5. Waste from the membrane chromatography process is directed to waste storage container 440 via conduit 510F. The purified product is directed to diafiltration component 320 for dialysis via conduit 510G and pump 520C.

Membrane chromatography component 310 may also include one or more sensors 312 for monitoring product quality parameters, such as conductivity, temperature, pH, oxygen, $CO_2$, absorbance, fluorescence, Raman, circular dichroism and infrared spectral characteristics. The sensors 312 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947. In addition, membrane chromatography component 310 preferably includes a heating and cooling element 314, suitably a thermoelectric cooler, for controlling the temperature of the solution (raw product) inside the membrane chromatography component 310.

The diafiltration component 320 may suitably include a hydrophilic polymeric membrane for use as a separation mode for dialysis for separating proteins in a diluent liquid on the basis of differences in their ability to pass through a membrane or in the alternative for diafiltration to simply exchange the buffer solutions. Such hydrophilic polymeric membrane may include, but not limited to, polyethersulfone, a cellulosic, or a polyvinylidene fluoride (PVDF) membrane with a well-defined pore structure that yields a desired molecular weight cut-off (MWCO) value in the range of 10 k to 200 k Da as appropriate for a given application. The final protein that comes out of the diafiltration component 320 is directed to product storage container 450 via conduit 510H. The waste product produced from the dialysis process in the diafiltration component 320 is directed to waste storage container 440 via conduit 510I.

Diafiltration component 320 may also include one or more sensors 322 for monitoring product quality parameters, such as conductivity, temperature, pH, oxygen, $CO_2$, absorbance, fluorescence, Raman, circular dichroism and infrared spectral characteristics. The sensors 322 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947.

In addition, diafiltration component 320 preferably includes a heating and cooling element 316, suitably a thermoelectric cooler, for controlling the temperature of the solution (raw product) inside the membrane chromatography component 320.

In addition to the pumps 520A, 520B and 520C, any number of valves or other hydraulic components, such as additional pumps, may be used throughout the system 700 to assist in controlling the flow of solution/product between the various components of the system 700.

Figure 4:
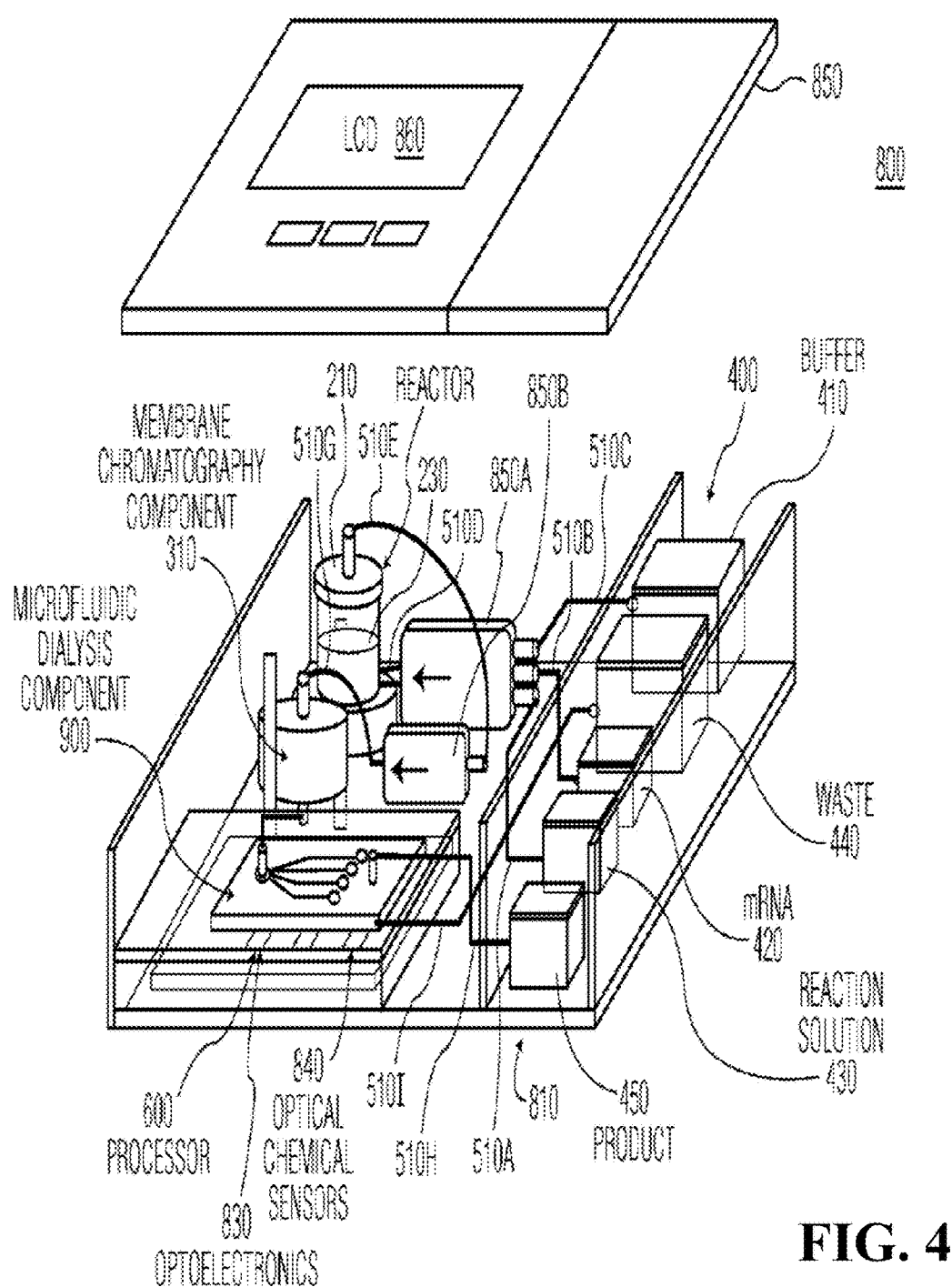
FIG. 4 is a schematic diagram of a microscale bioprocessing system, in accordance with another embodiment of the present invention.

The present invention is particularly suited to miniaturization by using micropumps and microfluidic technology. FIG. 4 is a schematic diagram of a microscale bioprocessing system 800, in accordance with another embodiment of the present invention. The system 800 includes many of the same components of the system 700 of FIG. 3, and common elements are labeled with common element numbers.

The system 800 contains a fluid storage/dispensing module 400 that includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. The system 800 also includes a reactor 210, a membrane chromatography component 310, a diafiltration component 820, a processor 600, optical chemical sensors 840 chosen and positioned to monitor finished product quality parameters, such as, for example, conductivity, redox, pH, UV spectrum and protein concentration, and optoelectronics 830 for providing optical excitation light and for detecting emission light from the optical chemical sensors 840. The optoelectronics 830 may also just be used to measure the optical properties of the finished product absent any sensors.

The reactor 210 can be of any size, but in the microscale embodiment of FIG. 4, it preferably has a volume capacity of less than approximately 50 milliliters, and more preferably approximately 20 milliliters or less, in order to keep the system 800 relatively compact. The reactor 210 may be implemented, for example, with the BioGenie minibioreactor system manufactured by Scientific Bioprocessing, Inc.

Micropumps 850A and 850B and conduits 510A-510I direct solution to the various components in a manner similar to pumps 520A, 520B and conduits 510A-510I in the system 700 of FIG. 3. Although not shown in FIG. 4, the reactor 210 contains optical chemical sensors and optoelectronics for monitoring parameters in the reactor solution 230 in a manner similar to system 700 of FIG. 3. The micropumps 850A and 850B may be implemented with any type of micropump known in the art such as, for example, the mp5 micropump or the mp6 micropump manufactured by Bartels Mikrotechnik.

The housing lid 850 may contain a display, such as an LCD display 860, that connects to the processor 600 and that can provide information about the system 800, such as, for example, diagnostic information, reaction parameters and/or finished product quality parameters, such as, for example, conductivity, redox, pH, UV spectrum and protein concentration.

The processor 600 in FIGS. 2, 3 and 4 may be implemented with a general purpose desktop computer or a general purpose laptop computer. In addition, the processor may be implemented with a tablet computer or smartphone, such as iOS or Android-based tablets and smartphones. However, processor 600 can also be implemented with a special purpose computer, programmed microprocessor or microcontroller and peripheral integrated circuit elements, ASICs or other integrated circuits, hardwired electronic or logic circuits such as discrete element circuits, programmable logic devices such as FPGA, PLD, PLA or PAL or the like. In general, any device on which a finite state machine capable of executing code for implementing the functionality described herein can be used to implement the processor 600.

Figure 5:
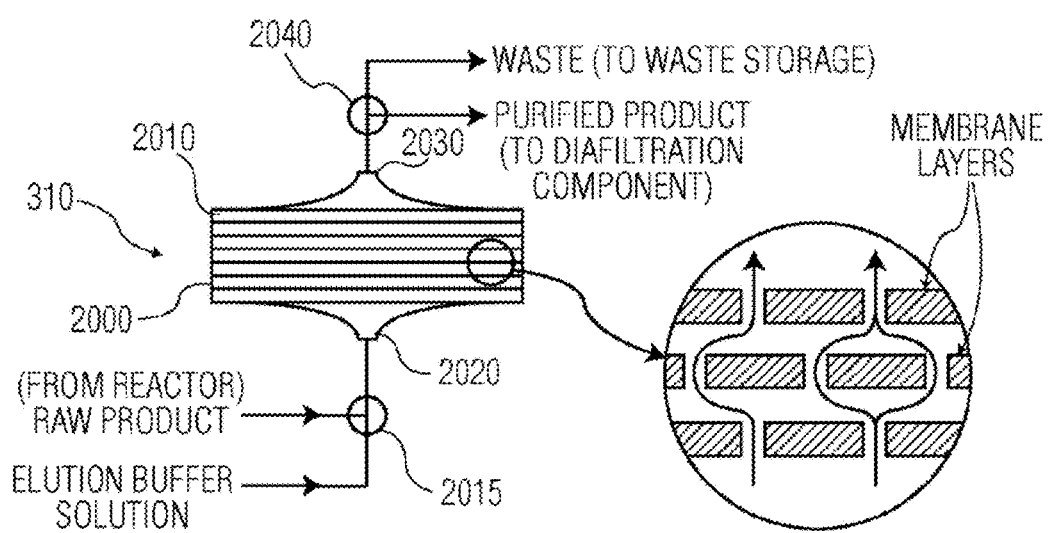
FIG. 5 is a side schematic view of a membrane chromatography component that can be used in the systems of FIGS. 3 and 4, in accordance with the present invention.

FIG. 5 shows a membrane chromatography component 310 that can be used in systems 700 and 800, in accordance with one preferred embodiment of the present invention. The membrane chromatography component 310 includes a housing 2000 and porous membrane layers 2010 (preferably at least 10 porous membrane layers). As discussed above, the individual porous membrane layers 2010 preferably consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography.

The membrane chromatography component 310 can be of any size, but in the microscale embodiment of FIG. 4, it preferably has a volume capacity of less than approximately 100 milliliters, and more preferably less than approximately 5 milliliters, in order to keep the system 800 relatively compact. The membrane chromatography component 310 may be implemented, for example, with a Sartobind® Q SingelSep Nano manufactured by Sartorius Stedim Biotech, which has a bed volume of 1 ml and a membrane area of 36 cm$^2$.

Raw product from reactor 210 is mixed with elution buffer solution via three-way valve 2015, and the mixture enters the membrane chromatography component 310 via inlet 2020. Purified product and waste exits via the outlet 2030. Three-way valve 2040 directs the purified product to the diafiltration component 320/900/1100 and directs the waste to waste storage 440.

Figure 6A:
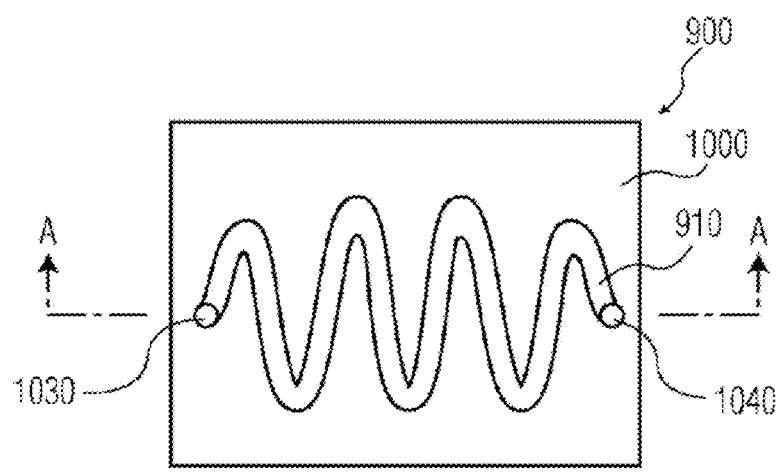
FIG. 6A is a top plan view of a microfluidic diafiltration component that can be used in the systems of FIGS. 3 and 4, in accordance with the present invention.
Figure 6B:
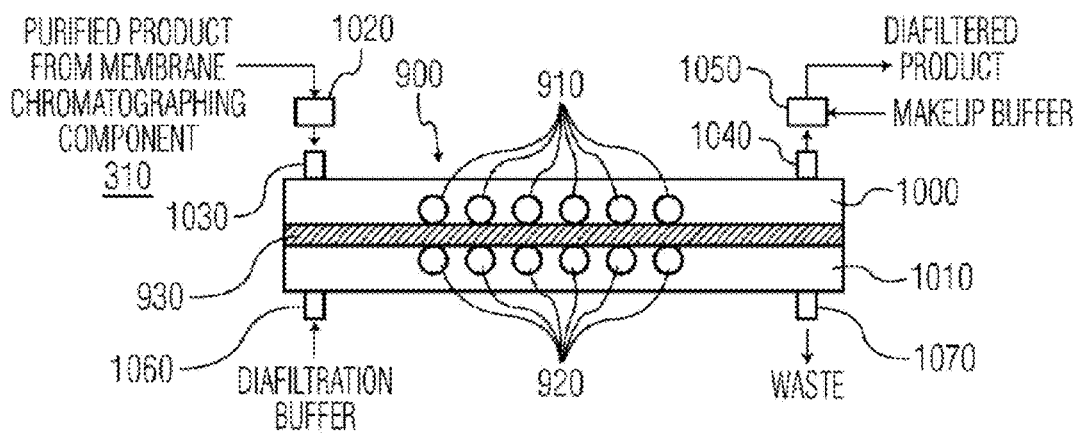
FIG. 6B is a schematic cross-sectional view of the equilibrium chamber of FIG. 6A looking along the cross-section line A-A of FIG. 6A.
Figure 6C:
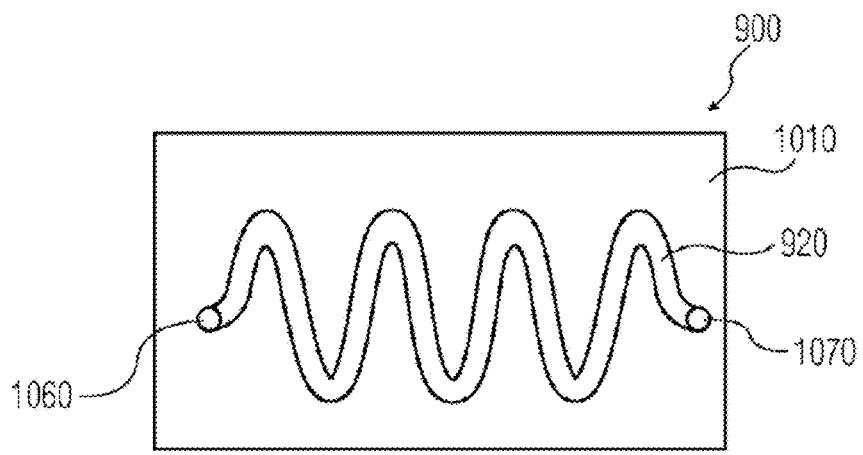
FIG. 6C is a bottom plan view of the equilibrium chamber of FIG. 6A.

FIGS. 6A-6C show a diafiltration component 900 that can be used in systems 700 and 800, in accordance with one preferred embodiment of the present invention. The diafiltration component 900 includes serpentine-shaped product and buffer sections 910 and 920, respectively. The diafiltration component 900 of FIGS. 6A-6C include a product section 910 that is a serpentine-shaped channel formed on a first substrate 1000. Similarly, the buffer section 920 is a channel formed on a second substrate 1010 with the same serpentine shape as the product section 910. A diafiltration membrane 930 is sandwiched between the first and second substrates 1000 and 1010, such that the serpentine-shaped channels that form the product and buffer sections 910 and 910 substantially overlap each other. The substrates 1000 and 1010 are attached to each other, with the diafiltration membrane 930 sandwiched between them, with any adhesive known in the art.

In the diafiltration component 900 of FIGS. 6A-6C, a diafiltration buffer solution flows through the serpentine-shaped product section 920 and purified product from the membrane chromatography component 310 flows through the serpentine-shaped product section 910. Diffusion takes place from the product section 910 to the counterpart, similarly shaped buffer section 920 via the diafiltration membrane 930.

The purified product from the membrane chromatography component 310 enters the product section 910 via inlet buffer reservoir 1020 and inlet 1030. The diafiltered product exits the product section 910 via outlet 1040 and outlet buffer reservoir 1050. Diafiltration buffer enters the buffer section 920 via inlet 1060 and exits the buffer section via outlet 1070. The diafiltration buffer is chosen to facilitate the transfer of components through the diafiltration membrane 930, and could be, for example, 25 millimolar phosphoric acid titrated to pH 7 with sodium hydroxide, or 25 millimolar citric acid tritrated to pH 5 with sodium hydroxide.

The inlet and outlet buffer reservoirs 1020 and 1050 are optionally used in order to dampen the back-and-forth oscillating flow, if needed. A makeup buffer solution is preferably added to the diafiltered product via the outlet buffer reservoir 1050 in order to replace the fluid that was that passed through the diafiltration membrane 930 with an equivalent volume of a different type of buffer, thereby transferring the protein of interest to the makeup buffer. Alternatively, the volume of the makeup buffer added via the outlet buffer reservoir 1050 can be less than the volume of fluid that has passed through the diafiltration membrane 930, in which case the diafiltration component 900 accomplishes both buffer exchange and protein concentration.

As discussed above, diafiltration membrane 930 may suitably be a hydrophilic polymeric membrane, such as a polyethersulfone, a cellulosic, or a polyvinylidene fluoride (PVDF) membrane with a well-defined pore structure that yields a desired molecular weight cut-off (MWCO) value in the range of 10 k to 200 kDa as appropriate for a given application.

Figure 7:
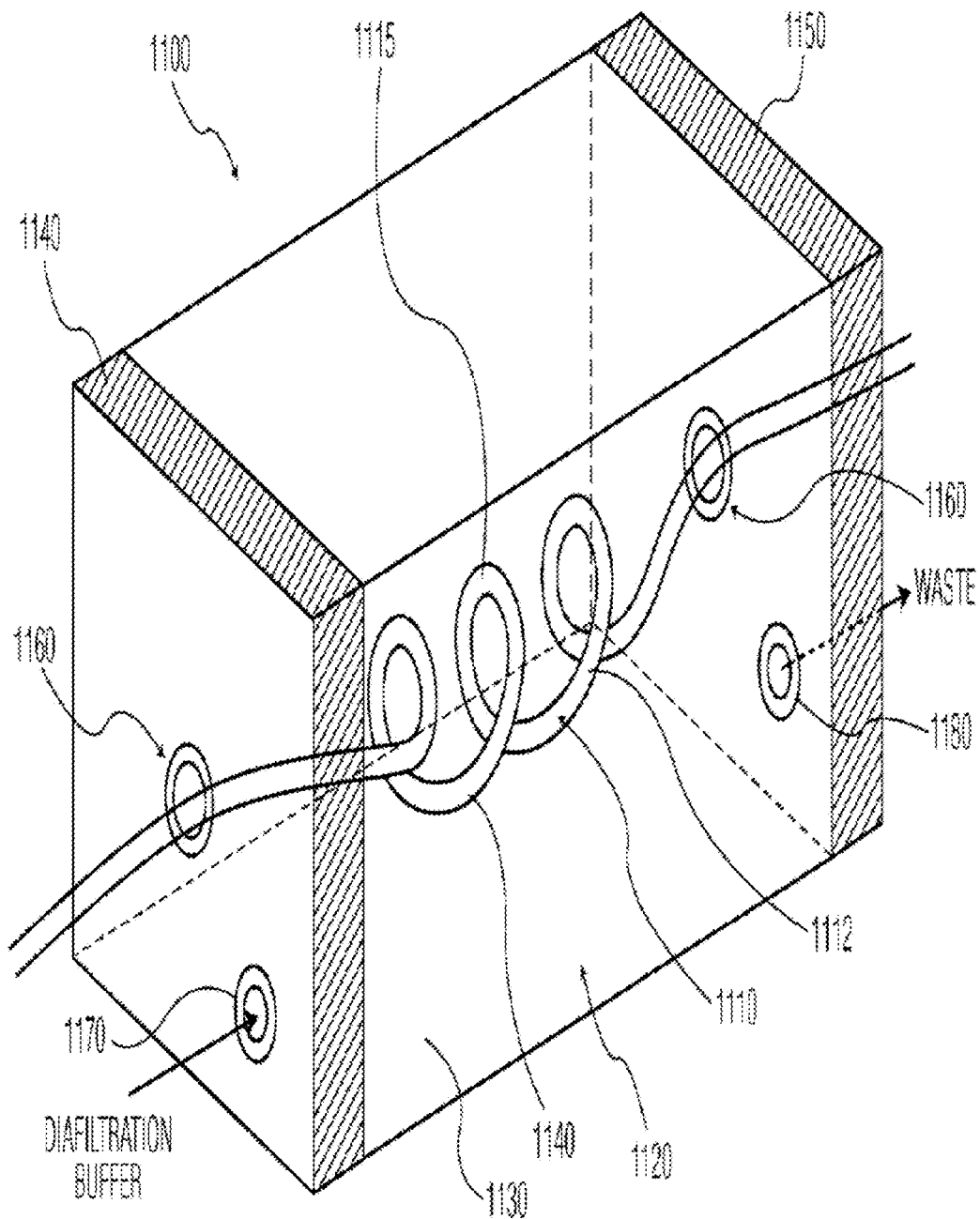
FIG. 7 is a perspective schematic view of another microfluidic diafiltration component that can be used in systems of FIGS. 3 and 4, in accordance with the present invention.

FIG. 7 shows a diafiltration component 1100 in accordance with another embodiment of the present invention. The diafiltration component 1100 may be used in system 700 or system 800 of FIGS. 3 and 4, respectively. The diafiltration component 1100 includes a buffer section 1120, and a product section 1110 that comprises tubing 1112 that is passed through the buffer section 1120. The tubing 1112 that makes up the product section 1110 can be any type of tubing known in the art that can function as the dialysis membrane 1140 between the product 1115 in the product section 1110 and the buffer 1130 in the buffer section 1120.

The tubing 1112 is preferably flexible so that a larger amount of tubing can be placed inside the solvent section 1120. The more tubing 1112 is present in the buffer section 1120, the more diffusion can take place between the tubing 1112 and the buffer 1130 due to the larger tubing surface area in contact with the buffer 1130. End portions 1140 and 1150 of the diafiltration component 1100 contain openings 1160 for the tubing 1112 to enter and exit the diafiltration component 1100. The end portions 1140 and 1150 also contain an inlet 1170 for receiving diafiltration buffer solution, and an outlet 1180 for expelling used diafiltration buffer solution (waste). Although the diafiltration component 1100 is shown as rectangularly-shaped, it can be any other shape, such as cylindrically-shaped. Further, the diafiltration component 1100 can suitably be a flow cell that has been modified to pass the tubing 1112 through the buffer section 1120.

Protein Expression in In Vivo and Cell-Free Systems

Figure 8:
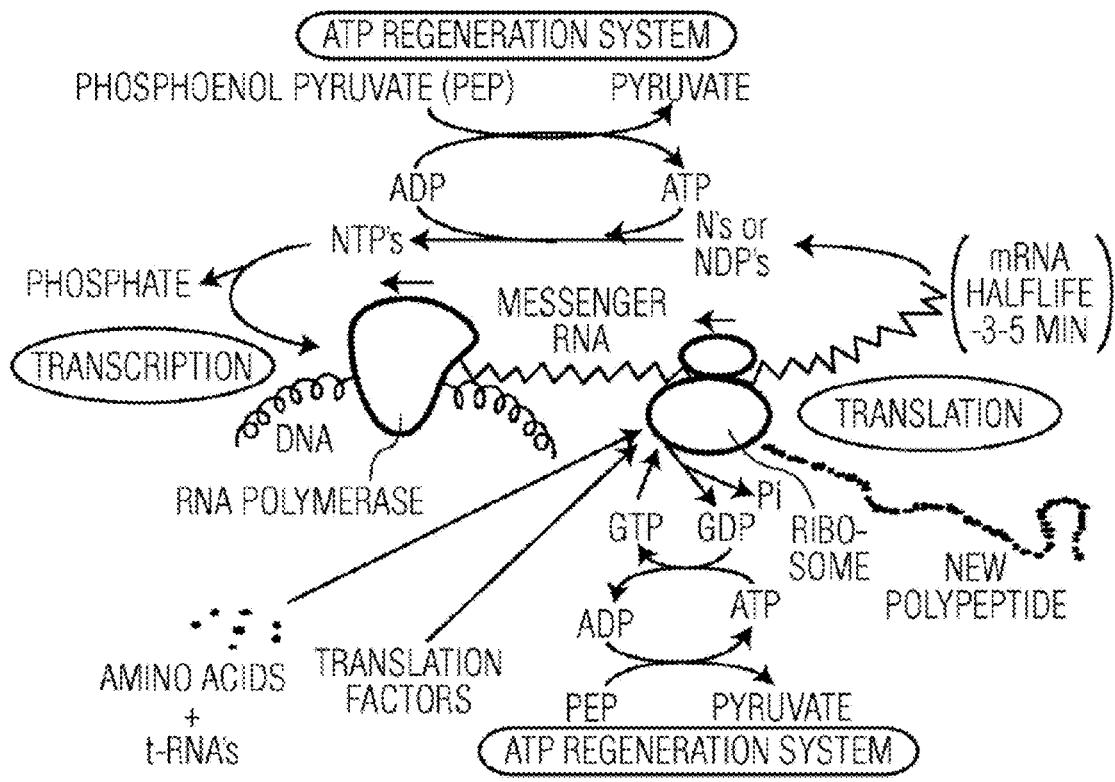
FIG. 8 is a diagram showing the main steps in in vivo protein expression.

A protein is expressed in three main steps: replication, transcription and translation, as shown in FIG. 8. DNA multiplies to make multiple copies by a process called replication. Transcription occurs when the double-stranded DNA is unwound to allow the binding of RNA polymerase producing messenger RNA (mRNA). Transcription is regulated at various levels by activators and repressors, and also by chromatin structure in eukaryotes. In prokaryotes, no special post-transcriptional modification of mRNA is required. However, in eukaryotes, mRNA is further processed to remove introns (splicing), to add a 'cap' (M7 methyl-guanosine) at the 5' end and to add multiple adenosine ribonucleotides at the 3' end of mRNA to generate a poly(A) tail. The modified mRNA is then translated.

The translation or protein synthesis is also a multi-step process with Initiation, Elongation and Termination steps and is similar in both prokaryotes and eukaryotes. The difference is that in eukaryotes, proteins may undergo post-translational modifications, such as phosphorylation or glycosylation. The translation process requires cellular components such as ribosomes, transfer RNAs (tRNA), mRNA and protein factors as well as small molecules like amino acids, ATP, GTP and other cofactors.

The difference between in vivo and in vitro (cell-free) protein expression is that in cell-free expression, the cell wall and the nuclei are no longer present.

Cell-Free Protein Expression from an Engineer's Perspective

To obtain the cell extract for cell-free protein expression, cells (E. coli, wheat germ, mammalian cells) are subjected to cell lysis followed by separation of the cell wall and nuclear DNA. The desired protein is synthesized by adding a DNA or mRNA template into the cell extract together with a reaction mix comprising of biological extracts and/or defined reagents. The reaction mix is comprised of amino acids, nucleotides, co-factors, enzymes and other reagents that are necessary for the synthesis, e.g. ribosomes, tRNA, polymerases, transcriptional factors, etc. When DNA is used as template (i.e. linked reaction), it is first transcribed to mRNA. Alternatively mRNA could also be used directly for translation.

The template for cell-free protein synthesis can be either mRNA or DNA. Translation of stabilized mRNA or combined transcription and translation converts stored information into a desired protein. The combined system, generally utilized in E. coli systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Salts, particularly those that are biologically relevant, such as manganese, potassium or ammonium, may also be added. The pH of the reaction is generally run between pH 6-9. The temperature of the reaction is generally between 20° C. and 40° C. These ranges may be extended.

In addition to the above components such as cell-free extract, genetic template, and amino acids, other materials specifically required for protein synthesis may be added to the reaction. These materials may include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol (DTT), ascorbic acid, glutathione and/or their oxides. Further DTT may be used as a stabilizer to stabilize enzymes and other proteins, especially if some enzymes and proteins possess free sulf-hydryl groups. Also, a non-denaturing surfactant such as Triton X-100 may be used at a concentration of 0-0.5 M. Spermine and spermidine may be used for improving protein synthetic ability, and cAMP may be used as a gene expression regulator.

Synthesized product is usually accumulated in the reactor within the production module, and then is isolated and purified according to the methods of the present invention for protein purification after completion of the system operation. The amount of protein produced in a translation reaction can be measured in various fashions. One method relies on the availability of an assay that measures the activity of the particular protein being translated. Examples of assays for measuring protein activity are a luciferase assay system and a chloramphenicol acetyl transferase assay system. These assays measure the amount of functionally active protein produced from the translation reaction. Importantly, activity assays will not measure full length protein that is inactive due to improper protein folding or lack of other post translational modifications necessary for protein activity. As used herein, the term "activity" refers to a functional activity or activities of a peptide or portion thereof associated with a full-length (complete) protein. Functional activities include, but are not limited to, catalytic or enzymatic activity, antigenicity (ability to bind or compete with a polypeptide for binding to an anti-polypeptide antibody), immunogenicity, ability to form multimers, and the ability to specifically bind to a receptor or ligand for the polypeptide. Preferably, the activity of produced proteins retain at least 55%, 60%, 65%, 70%, 80%, 85%, 90%, 95% or more of the initial activity for at least 3 days at a temperature from about 0° C. to 30° C.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products.

In another study, expression of a fusion protein consisting of murine GM-CSF (granulocyte macrophage colony stimulating factor) and a scFv antibody, in reactor systems such as thin film, bubble column and Eppendorf tube without membrane, were studied, producing protein up to >500 μg/ml protein with significant amount of precipitated protein (apprx eq. 50%). Recently, rhGM-CF was expressed in a 100 L stirred tank reactor expressing protein up to 700 mg/L which was subsequently purified with DEAE resin, tangential flow filtration membrane (3 kD cut off) and Sephacryl S-100 size exclusion chromatography with 99% purity and 65% recovery. Cell-free expression has not only been successful in the expression of bacterial proteins, but also successfully produced glycoproteins like human choriogonadotropin (hCG) and envelope glycoprotein (gp120) of human immunodeficiency virus type-1 (HIV-1) in hybridoma cell extract (HF10B4).

For protein purification, people have relied on column chromatography traditionally, but in recent years membrane chromatography has emerged as an additional aid in this field, eliminating column chromatography at specific steps like capture and polishing of protein at final step with overall cost reduction up to 65%. Column chromatography is still useful for gradient purification of proteins, but membrane chromatography could also be studied by relying on the fact that step elution of protein and removal of the impurities could be done at different buffer conditions.

The chart below compares cell-free and in vivo protein expression systems.

| In vivo | Cell free |
| --- | --- |
| Biological cell required | No cell, but cellular machinery is required |
| Time consuming process | Time effective process |
| Toxic protein may be difficult to express | Toxic protein could be expressed |
| Multiple steps in purification required | Relatively less number of steps required |
| Higher fraction of misfolded protein along with folded protein | Reduced levels of misfolded protein reported, along with folded protein but precipitated |
| Higher endotoxins challenge | Relatively less endotoxins challenge |
| Higher amount of impurities in crude protein causing challenges in capture step | Relatively less impurities, enhancing capture and increasing yield of the protein |
| Established scale up | Has significant potential to scale up |
| Protein expression up to g/l | Protein expression up to mg/l |

Biomolecules for Protein Expression

The following biomolecules are preferably used for protein expression. To carry out a protein expression reaction, energy components and amino acids are supplied externally and may include, but not limited to the following components:

a. A genetic template for the target protein (mRNA or DNA) expression;
b. T7 RNA polymerases for mRNA transcription;
c. 9 Translation factors (initiation, elongation and termination);
d. 20 aminoacyl-tRNA synthetases (ARSes) for esterification of a specific amino acid to form an aminoacyl-tRNA;
e. Methionyl-tRNA transformylase transfers hydroxymethyl-, formyl-groups;
f. Creatine kinase converts ATP to ADP;
g. Myokinase catalyzes the inter conversion of adenine nucleotides;
h. Pyrophosphatase are acid anhydride hydrolases that act upon diphosphate bonds;
i. 4 nucleoside triphosphates (ATP, GTP, CTP, TTP) for DNA formation;
j. Creatine phosphate which serves as a reserve of high-energy phosphates for rapid mobilization;
k. 10-formyl-5,6,7,8-tetrahydrofolate for the formylation of the methionyl initiator tRNA (fMet-tRNA);
l. 20 amino acids for protein synthesis;
m. Ribosomes for polypeptide translation;
n. 46 tRNAs in protein synthesis; and
o. Cellular components which assist in proper protein folding.

Some of the proteins that may be expressed by the present invention for on-demand production may include, but not limited to, adrenocorticotropic hormone peptides, adrenomedullin peptides, allatostatin peptides, amylin peptides, amyloid beta-protein fragment peptides, angiotensin peptides, antibiotic peptides, antigenic polypeptides, anti-microbial peptides, apoptosis related peptides, atrial natriuretic peptides, bag cell peptides, bombesin peptides, bone GLA peptides, bradykinin peptides, brain natriuretic peptides, C-peptides, C-type natriuretic peptides, calcitonin peptides, calcitonin gene related peptides, CART peptides, casomorphin peptides, chemotactic peptides, cholecystokinin peptides, colony-stimulating factor peptides, corticortropin releasing factor peptides, cortistatin peptides, cytokine peptides, dermorphin peptides, dynorphin peptides, endorphin peptides, endothelin peptides, ETa receptor antagonist peptides, ETh receptor antagonist peptides, enkephalin peptides, fibronectin peptides, galanin peptides, gastrin peptides, glucagon peptides, Gn-RH associated peptides, growth factor peptides, growth hormone peptides, GTP-binding protein fragment peptides, guanylin peptides, inhibin peptides, insulin peptides, interleukin peptides, laminin peptides, leptin peptides, leucokinin peptides, luteinizing hormone-releasing hormone peptides, mastoparan peptides, mast cell degranulating peptides, melanocyte stimulating hormone peptides, morphiceptin peptides, motilin peptides, neuro-peptides, neuropeptide Y peptides, neurotropic factor peptides, orexin peptides, opioid peptides, oxytocin peptides, PACAP peptides, pancreastatin peptides, pancreatic polypeptides, parathyroid hormone peptides, parathyroid hormone-related peptides, peptide T peptides, prolactin-releasing peptides, peptide YY peptides, renin substrate peptides, secretin peptides, somatostatin peptides, substance P peptides, tachykinin peptides, thyrotropin-releasing hormone peptides, toxin peptides, vasoactive intestinal peptides, vasopressin peptides, and virus related peptides.

Conventional and Non-Conventional Method of GBP Production

The systems and methods of the present invention can be used, for example, for the cell-free expression and purification of glucose binding protein (GBP). Glucose is a major carbon and energy source in cellular metabolism of animal body and in bioprocess industry. Glucose is not always beneficial in bioprocesses, it could also be detrimental in bacterial culture leading to self-lysis of cells by formation of acetate in Krebs cycle and reducing the pH of the culture. Thus, fast and efficient concentration detection of glucose is desired.

Glucose binding protein is a protein which could bind to glucose and serve this purpose by acting as a biosensor. A biosensor is an analytical device used for the detection of an analyte that combines a biological component with a physicochemical detector component. GBP is such a biosensor, where GBP binds with glucose and binding is analyzed using fluorescence intensity and the corresponding signal is compared with standard glucose signal to estimate concentration of unknown sample. GBP is a monomeric periplasmic protein with molecular weight of 34 kD (kilo Dalton) and is synthesized in the cytoplasm of E. coli.

In the conventional method, GBP (L225C mutant) is produced in multiple steps, pre-inoculation of E. coli mutants in Luria Bertani (LB) broth, culturing, harvesting, cell washing, osmotic shock, labeling, liquid chromatography and dialysis. All these steps are time consuming (around 4 days) and cumbersome. The present invention enables a non-conventional cell free expression of GBP where expression is faster and the resulting protein is relatively pure. This protein would preferably be labeled using a fluorophore called acrylodan (6-Acryloyl-2-dimethylaminonaphthalene) and purified by D15 (DEAE) chromatography membrane. The protein would preferably further be concentrated and dialyzed against 5 mM tris-HCl, pH 7.5.

Cell Free Method of Production of Granulocyte Colony Stimulating Factor (G-CSF) and Pharmaceutical Analog Fligrastim For proof of principle, G-CSF also known as the pharmaceutical analog Filgrastim is used as a model therapeutic protein. Notably, the same method holds for any therapeutic protein for administration at the point-of-care. Filgrastim is used to stimulate the production of granulocytes (a type of white blood cell) in patients undergoing cancer therapy with specific drugs that are known to cause low white blood cell counts.

Cell-free protein synthesis system was tested for G-CSF protein expression, the DNA used as the template in the system was G-CSF plasmid: 80 µg (concentration: 0.47 µg/µL) in combination with lyophilized CHO lysate in an amount of 1 mL, Gadd34-Myc plasmid 8 ug (@0.4 ug/uL) =20 uL)), Thermo Reaction Mix (5×): 400 uL, nuclease free water: balance to 2 mL, and 1×CHO dialysis buffer at 25 mL. Six batches were run with a total batch volume for each batch of about 2 mL and the process took about 6 hours at a temperature of about 30° C. The bioreactor used was SLIDE-A-LYZER™ dialysis cassette (10 kDa cutoff: 3 mL).

About 1.98 mL of harvested product was subjected to purification in an IMAC spin column with loading buffer: 10 mM imidazole, wash buffer 1: 10 mM imidazole, wash buffer 2: 30 mM imiadazole and elution buffer: 150 mM imidazole. Notably PBS buffer, without DTT, was used in the purification process. The fractions were collected from triplicate runs where G-CSF was expressed over a six hour period in the presently claimed cell-free system. The G-CSF was purified using a His-tagged affinity column. The data show the remarkable consistency of the expression and purification of the target product.

Figure 9A:
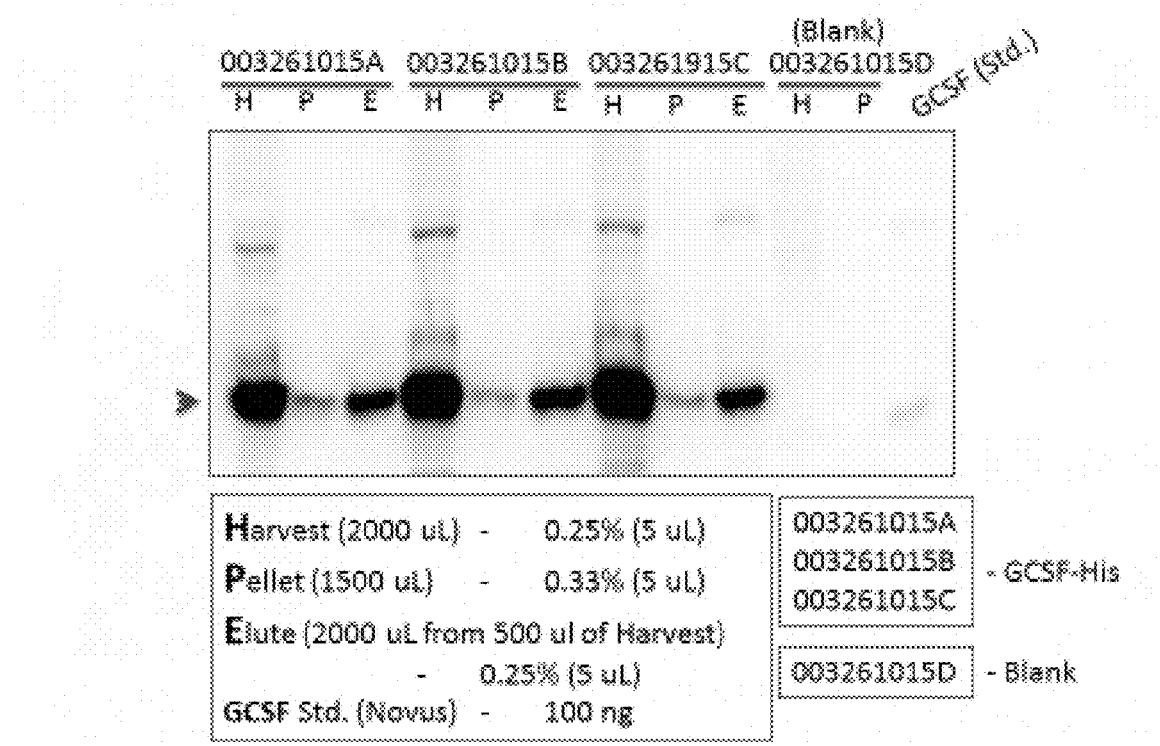
FIG. 9A shows results for the expression of G-CSF from different runs (Run #3) and showing the reproducibility.
Figure 9B:
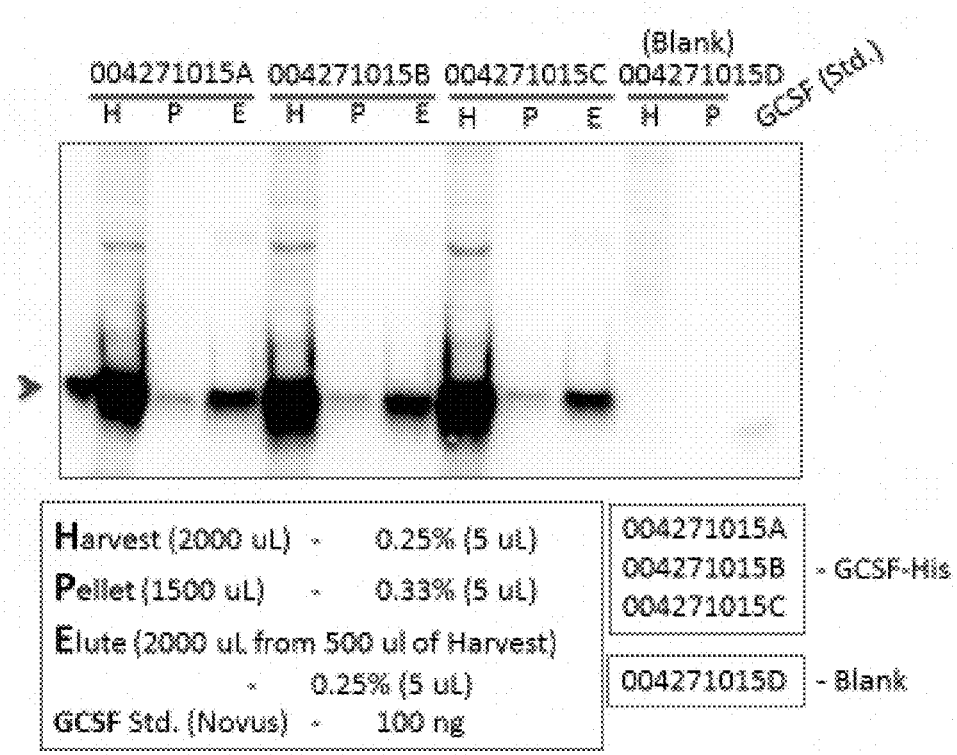
FIG. 9B shows results for the expression of G-CSF from different runs (Run #4) and showing the reproducibility.

FIGS. 9A and 9B show Western Blot results with an Anti-G-CSF antibody. The pellets discussed in both figures were washed once with 500 µL of PBS and solubilized in 1500 µL of PBS with 1% Tween-20 and 1.5% Triton X-100. The "H" represents the Harvest, the "P" is the Pellet and the "E" is the Elute. The elution column shows a clear band representing G-CSF for all three runs showing the remarkable consistency of the expression and purification of the target product. The far right column shows the G-CSF standard that was also run. FIG. 9A shows the results of Run #3 and FIG. 9B shows the results of Run #4. Clearly the results are consistent and provide evidence that the process of the present invention is reproducible.

Figure 10A:
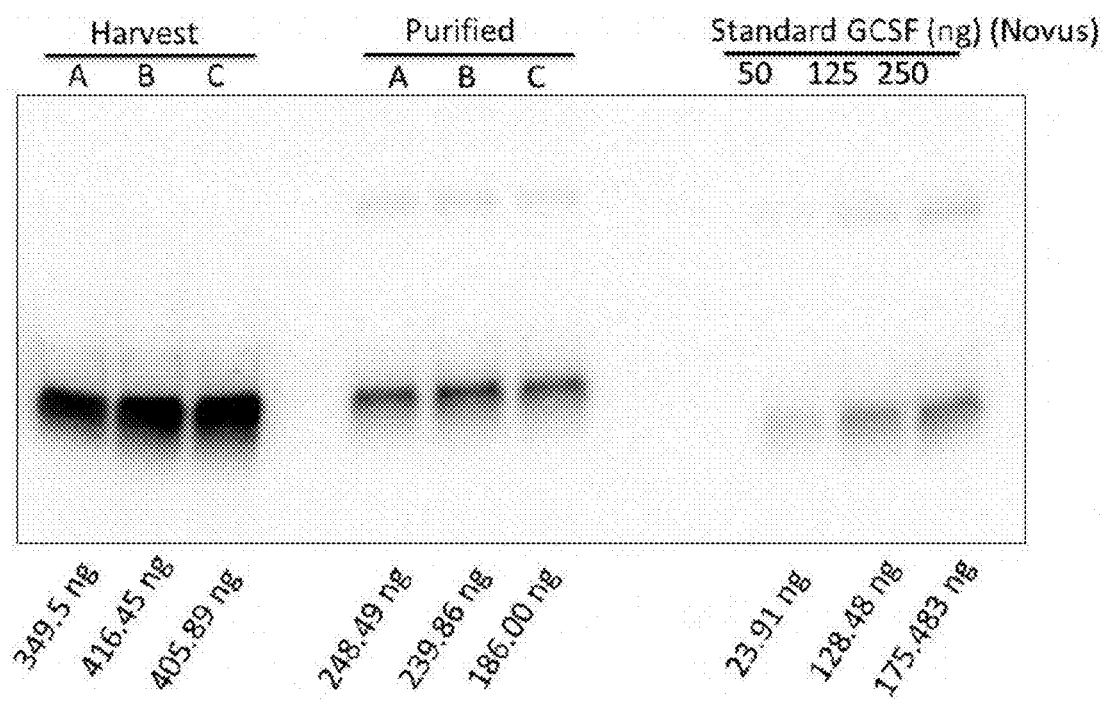
FIG. 10A shows the quantified values for Run#3 of FIG. 9A.
Figure 10B:
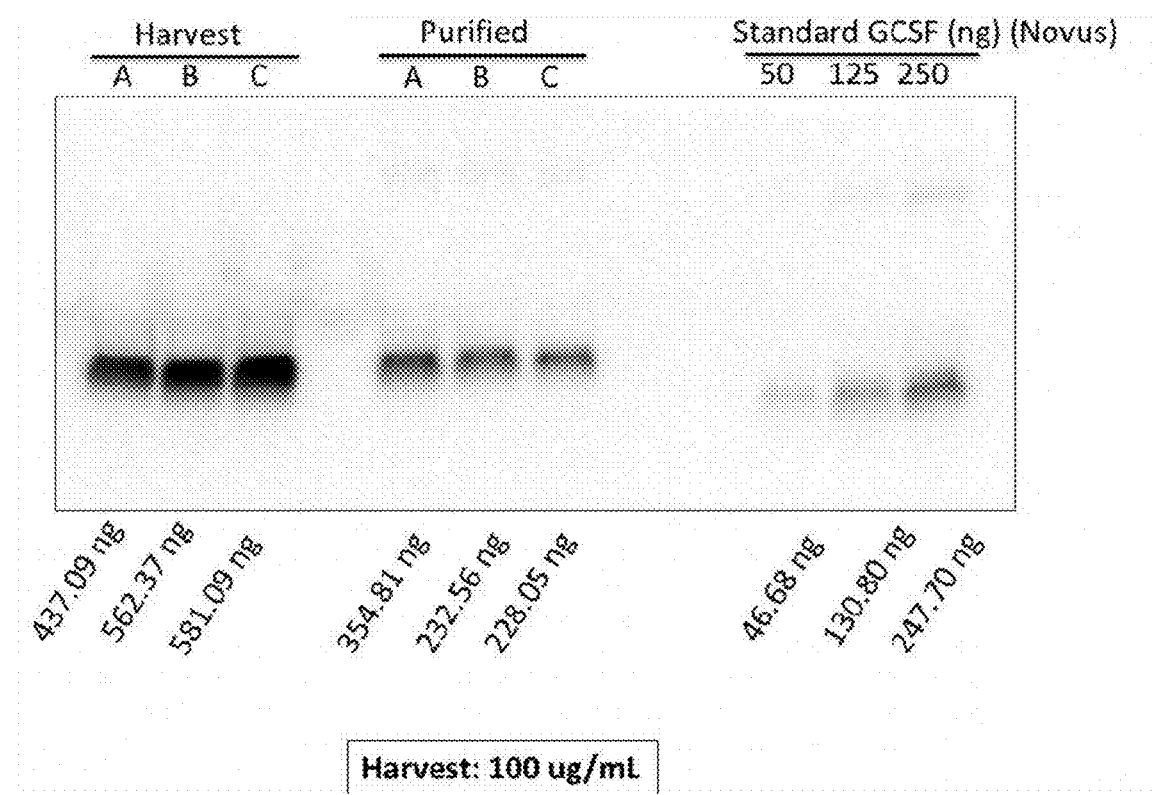
FIG. 10B shows the quantified values for Run#4 of FIG. 9B.

FIG. 10 A shows the quantified values of the harvested proteins and purified protein of Run #3 of FIG. 9A and FIG. 10B show the values of Run#4 of FIG. 9B.

Figure 11:
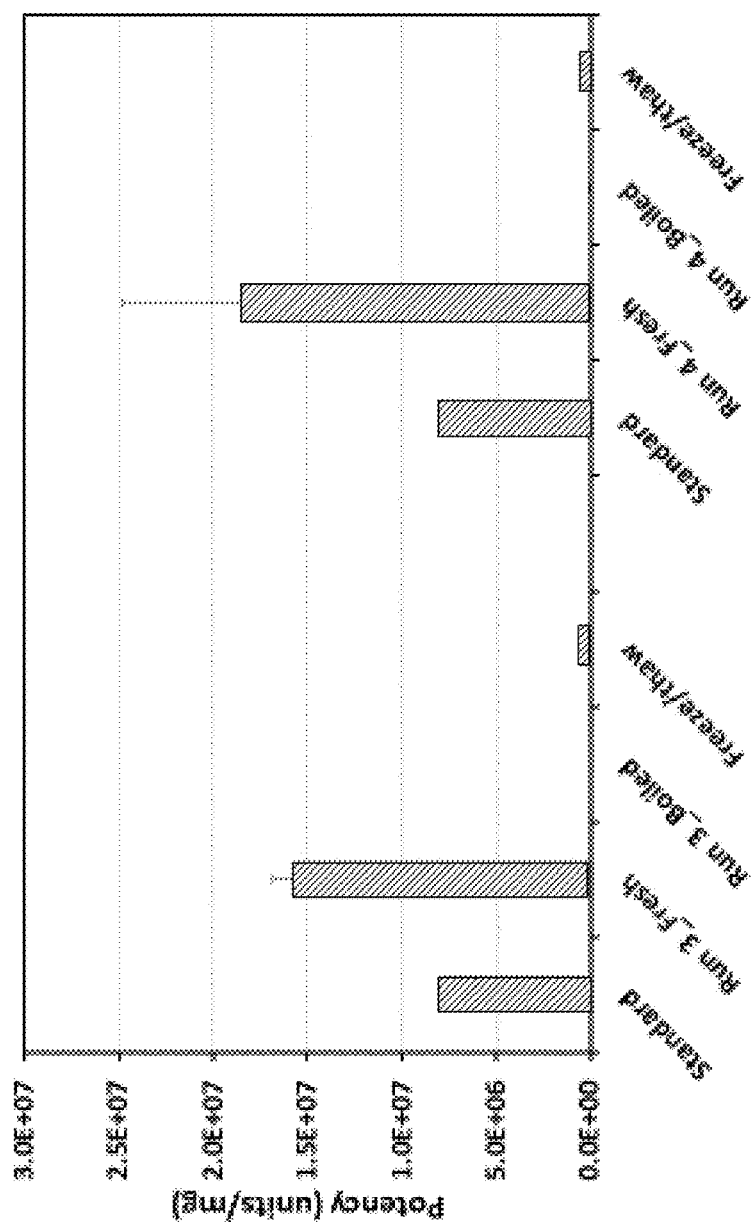
FIG. 11 shows the potency results of recombinant human G-CSF from Run #3 and Run #4.

Further it was shown that proteins produced in the on-demand system of the present invention provide for improved and increased potency relative to freeze/thaw data of the prior art method and it is evident that using a freeze/thaw cycle impacts activity. As shown in FIG. 11, in the results of separate runs of 3 and 4, it can be seen that the freshly made G-CSF has potency twice that of the reconstituted lyophilized standard. The same molecule loses its potency after just one freeze-thaw cycle approaching that of a boiled control. These data prove our assertion that administering a freshly made therapeutic protein (at most, refrigerated for a few days) provides maximal potency and has the additional advantage of no additives. This is a significant and surprising improvement over the current paradigm of biologics production and delivery.

Figure 12:
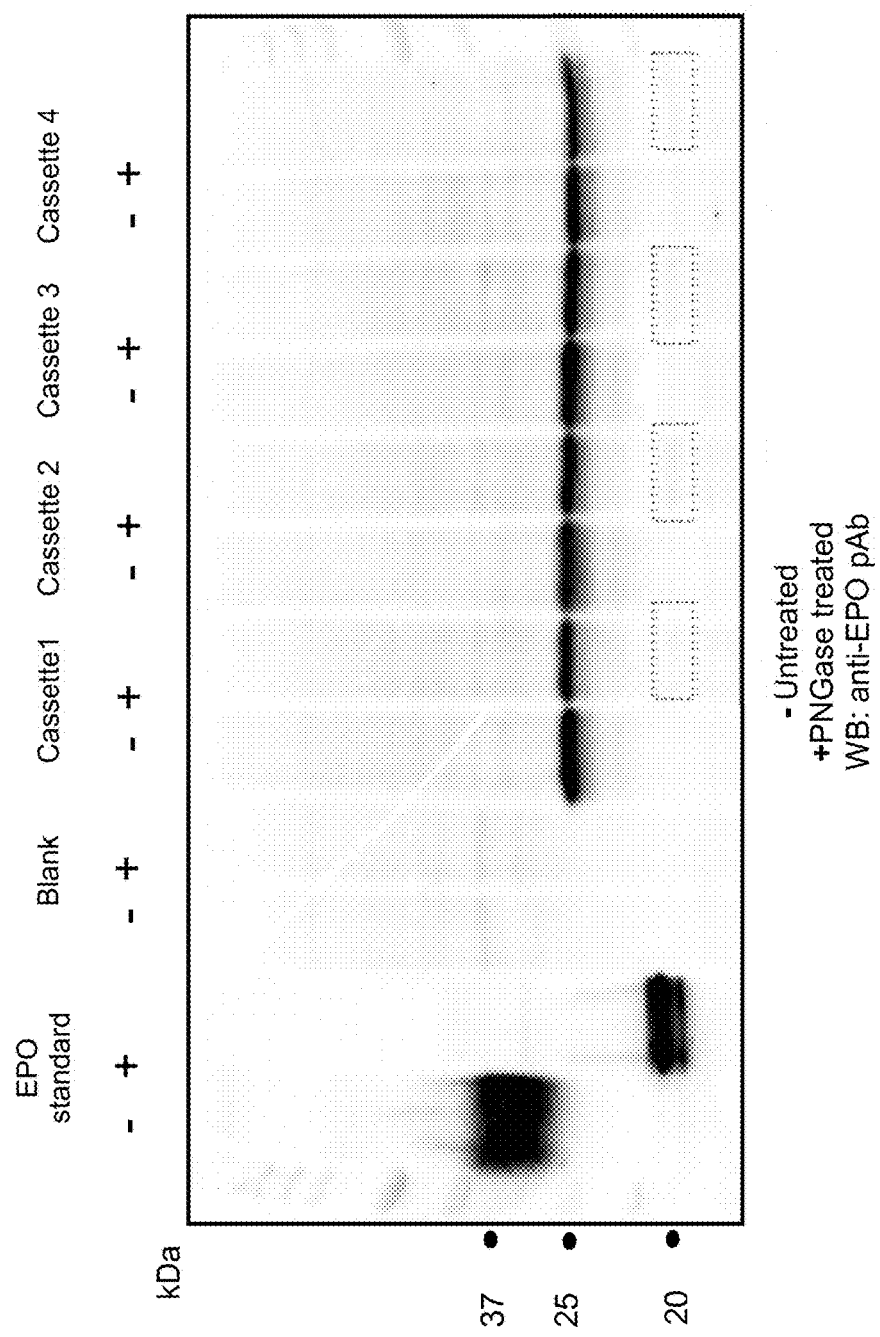
FIG. 12 shows the Western blot of quadruplicate run of EPO in dialysis cassettes prior to purification.

In another example, the therapeutic protein Erythropoetin (EPO, used to stimulate red blood cell production in the human body) was produced in the cell free system. FIG. 12 shows the same consistency of expression in 4 separate batches as evidenced by the bands on the Western blot.

Figure 13A:
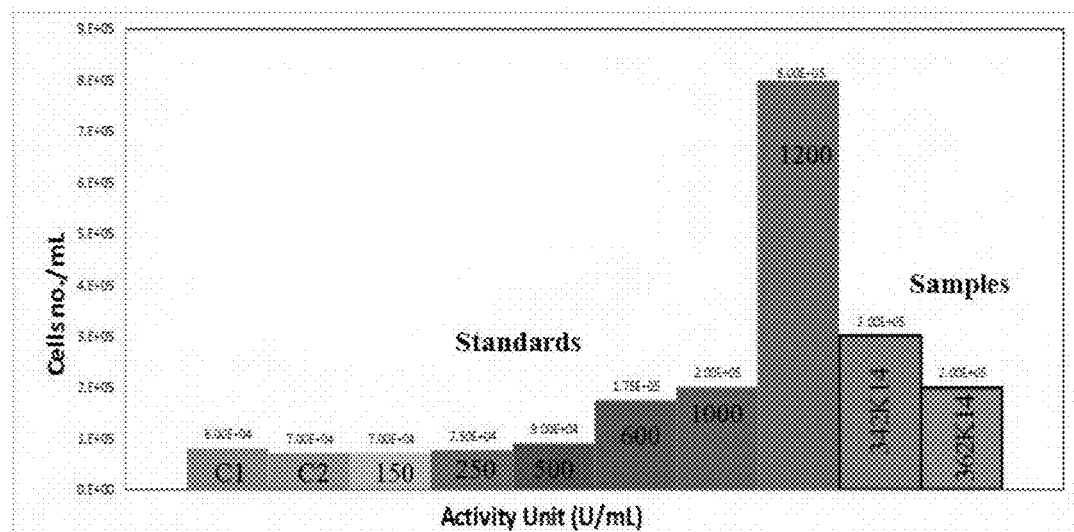
FIG. 13 A shows EPO expression in stirred tank bioreactor and FIG. 13 B shows Streptokinase expression in stirred tank bioreactor.

As the cell proliferation-based activity assay shows in the top panel of FIG. 13A, the EPO in the extract is more active compared to controls. It should be noted that the EPO tested from the cell free process was diluted 100-fold, so the activity in the extract was in excess of 100,000 units/mL. Given the typical EPO dosage is between 50-100 units/mL/kg, it appears that 1 mL product contains sufficient EPO to dose 10 adults. These data show the remarkable potential of point-of-care manufacturing as the freshly expressed protein shows very high activity. This is likely due to virtually no "aging" of the protein that normally takes place in conventionally manufactured proteins (i.e. deamidation, oxidation, aggregation etc.).

Figure 13B:
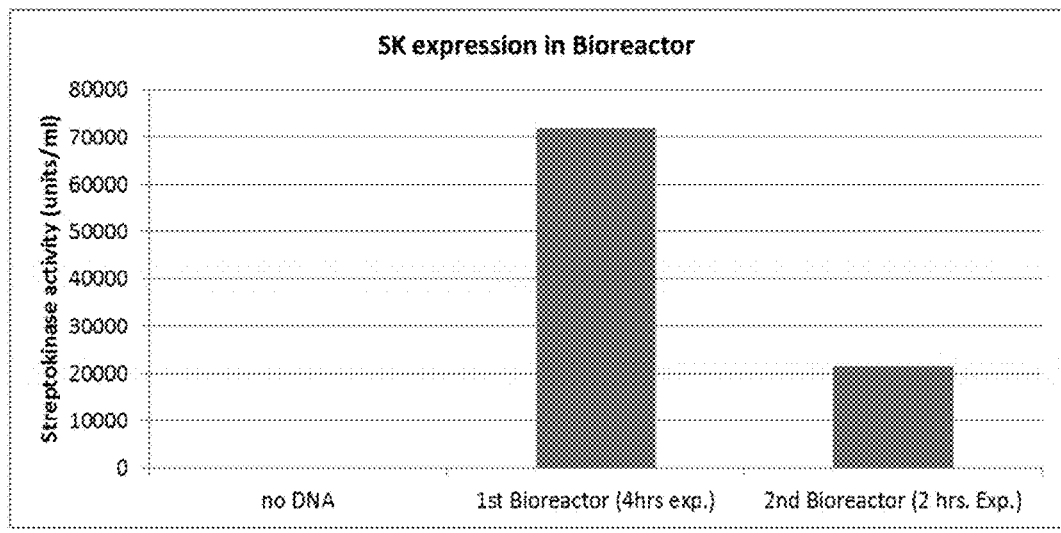

Streptokinase was also produced successfully in a cell free stirred tank bioreactor. A representative sample of activity at two harvest times is shown in FIG. 13B, lower panel. As can be seen, the harvest time may be used to pick a desired activity in the case of Streptokinase, several dosing regimens are in use clinically and the harvest can be timed to conform to the desired dose, eliminating any dilution for the final delivery to obtain the correct dose. As can be seen, active EPO was produced and had extremely high activity (samples 32K14 and 36K14 were diluted 100 fold for the assay). For Streptokinase, lysate was harvested at two time points and activity measured. This approach may be used to determine the dose needed for delivery to the patient.

That which is claimed is:

1. A method of delivering freshly synthesized therapeutic protein exhibiting increased activity and potency to a patient, said method comprising:
   delivering an on-demand cell-free synthesized therapeutic protein to a patient in need of said therapeutic protein, wherein said therapeutic protein is synthesized using a portable bioprocessing system comprising:
      a production module for producing the therapeutic protein, and
      a purification module for receiving the therapeutic protein from the production module and for purifying the therapeutic protein from reagents, wherein the purification module comprises:
         a chromatography component for receiving the therapeutic protein from the production module and for outputting purified therapeutic protein; and
         a diafiltration component for receiving the purified therapeutic protein from the chromatography component and for outputting further purified therapeutic protein, wherein the diafiltration component comprises a product section for receiving the purified therapeutic protein from the chromatography component and a buffer section for receiving a buffer solution.

2. The method of claim 1, wherein the therapeutic protein is produced in a composition with no or reduced amounts of stabilizers, oxidation/reduction agents and/or other excipients.

3. The method of claim 1, wherein the therapeutic protein is delivered to the patient in need of such protein within one hour after purification.

4. The method of claim 1, wherein the therapeutic protein is delivered to the patient in need of such protein within one day after purification.

5. The method of claim 1, wherein the therapeutic protein is delivered continuously or as a bolus to the patient in need of the protein.

6. The method of claim 1, wherein the therapeutic protein is refrigerated at an above-freezing temperature from 0° C. to 6° C. after purification but prior to delivery.

7. The method of claim 1, wherein a reaction mixture comprising a nucleotide template for production of a protein; monomers for the protein to be synthesized, co-factors, enzymes and reagents that are necessary for the synthesis can be introduced to the production module.

8. The method of claim 7, wherein the enzymes and reagents that are necessary for the synthesis are ribosomes, tRNA, polymerases and transcriptional factors.

9. The method of claim 7, wherein the reaction mixture is maintained at a pH between pH 6-9 during production of the therapeutic protein.

10. The method of claim 7, wherein the reaction mixture is maintained at a temperature between 20° C. and 40° C. during production of the therapeutic protein.

11. The method of claim 1, wherein the diafiltration component further comprises: a first substrate; a second substrate; and a diafiltration membrane positioned between the first and second substrates.

12. The method of claim 1, wherein the diafiltration component comprises a flow cell.

13. The method of claim 1, wherein the production module comprises at least one sensor for monitoring reaction parameters.

14. The method of claim 13, wherein the at least one sensor monitors at least one of conductivity, temperature, pH, oxygen and $CO_2$.

15. The method of claim 13, wherein the at least one sensor comprises an optical chemical sensor.

16. The method of claim 1, wherein the production module and purification module each comprise a heating and cooling element for controlling the temperature of solution inside the production module and purification module.

17. The method of claim 1, further comprising a fluid storage and dispensing module for storing solutions used by the production module for protein expression and for storing waste product produced by the purification module.

18. The method of claim 17, wherein the fluid storage and dispensing module also stores purified therapeutic protein output by the purification module.

19. The method of claim 1, wherein the portable bioprocessing system further comprises a processor for controlling and/or monitoring at least one of the production module and the purification module.

20. The method of claim 1, wherein potency/activity of the therapeutic protein is determined by the expression time in the production module.

21. The method of claim 1, wherein potency/activity of the therapeutic protein is determined by the holding time in the purification module.

* * * * *